US005556784A

United States Patent [19]
Liu

[11] Patent Number: 5,556,784
[45] Date of Patent: Sep. 17, 1996

[54] *BACILLUS THURINGIENSIS* ISOLATES ACTIVE AGAINST LEPIDOPTERAN PESTS

[75] Inventor: Chi-Li Liu, Davis, Calif.

[73] Assignee: Novo Nordisk Entotech, Inc., Davis, Calif.

[21] Appl. No.: 157,363

[22] Filed: Nov. 23, 1993

Related U.S. Application Data

[63] Continuation-in-part of Ser. No. 981,048, Nov. 24, 1992, abandoned.

[51] Int. Cl.$^6$ .............................. C12N 1/20; A01N 63/00
[52] U.S. Cl. ................ 435/252.5; 435/832; 424/93.461
[58] Field of Search ........................ 435/252.5, 252.31, 435/832; 424/93 L, 93.461; 514/2

[56] References Cited

U.S. PATENT DOCUMENTS

| | | | |
|---|---|---|---|
| 4,990,332 | 2/1991 | Payne et al. | 424/93 |
| 5,045,469 | 9/1991 | Payne et al. | 435/252.3 |
| 5,169,629 | 12/1992 | Payne et al. | 424/93 L |
| 5,188,960 | 2/1993 | Payne et al. | 435/252.3 |
| 5,206,166 | 4/1993 | Payne et al. | 435/252.3 |
| 5,246,852 | 9/1993 | Payne et al. | 435/252.31 |
| 5,268,172 | 12/1993 | Payne et al. | 424/93 L |
| 5,336,492 | 8/1994 | Payne et al. | 424/93.2 |
| 5,352,661 | 10/1994 | Payne et al. | 424/93.2 |
| 5,407,825 | 4/1995 | Payne et al. | 435/252.34 |

FOREIGN PATENT DOCUMENTS

| | | |
|---|---|---|
| 0256553 | 2/1988 | European Pat. Off. . |
| 62-129207 | 6/1987 | Japan . |
| 63-137684 | 6/1988 | Japan . |
| 1104177 | 4/1989 | Japan . |
| WO90/06999 | 6/1990 | WIPO . |

OTHER PUBLICATIONS

Hofte, H., et al., "Microbiological Reviews," vol. 53, Jun. 1989, pp. 242–255.
Padua, L. E., et al., "FEMS Microbiology Letters," vol. 66, 1990, pp. 257–262.
Shimizu et al., Agric. Biol. Chem., vol. 52, No. 6, pp. 1565–1573 (1988).
Schnepf et al., J. of Biol. Chem., vol. 260, No. 10, pp. 6264–6272 (May 1985).
Tailor et al., Mol. Microbiol., vol. 6, No. 9, pp. 1211–1217 (1992).
Feitelson et al., Bio/Technology, vol. 10, pp. 271–275 (Mar. 1992).
Luthy et al., B. Thuringiensis as a Bactl. Insecticide Basic Considerations and Application (Chapter 2); pp. 35–74 (1982).
Aronson et al., Microbiol. Reviews, vol. 50, pp. 11–24 (1986).
Adang et al., Gene, vol. 36, pp. 289–300 (1985).

*Primary Examiner*—Marian C. Knode
*Assistant Examiner*—K. Larson
*Attorney, Agent, or Firm*—Steve T. Zelson, Esq.; Cheryl H. Agris, Esq.

[57] ABSTRACT

The invention relates to a *Bacillus thuringiensis* strain(s) which solely produces a CryIA(a) crystal delta-endotoxin having a molecular weight of 130,000 daltons and is active against lepidopteran pests. The invention is also related to a spore(s), mutant(s), or crystal delta-endotoxin obtainable therefrom. Furthermore, the invention relates to insecticidal compositions comprising the *B.t.* strain, spore, mutant or crystal delta-endotoxin of the present invention. The invention further relates to methods of using the insecticidal compositions to control an insect pest(s) of the order Lepidoptera.

3 Claims, 1 Drawing Sheet

1 2 3 4 5 6 7 8 9 10 11 12 13 14

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE:- cDNA ( x i ) SEQUENCE DESCRIPTION: SEQ ID NO:1:

```
CTGCTCCAGC TGCTTGGCTC                                           20
```

( 2 ) INFORMATION FOR SEQ ID NO:2:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

GAATTATACT TGGTTCAGGC CC                                                    22

( 2 ) INFORMATION FOR SEQ ID NO:3:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

GCACACCTTA CATTTTAAAG CA                                                    22

( 2 ) INFORMATION FOR SEQ ID NO:4:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

AGATTACAAG CGGATACCAA CATCGCG                                               27

( 2 ) INFORMATION FOR SEQ ID NO:5:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

TGGCACTTTC AAAATAACCA A                                                     21

( 2 ) INFORMATION FOR SEQ ID NO:6:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

GCATCGGATA GTATTACTCA ATCCC                                                 25

( 2 ) INFORMATION FOR SEQ ID NO:7:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

CGGGATCCTG GGTCAAAAAT TGATATTTAG TAAAATTAG                                  39

5,556,784

13

-continued

14

( 2 ) INFORMATION FOR SEQ ID NO:8:

( i ) SEQUENCE CHARACTERISTICS:
( A ) LENGTH: 43 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:8:

CCTGTCGACT AGAAAATAAC ATAGTAAAAC GGACATCACT CCG 43

( 2 ) INFORMATION FOR SEQ ID NO:9:

( i ) SEQUENCE CHARACTERISTICS:
( A ) LENGTH: 3826 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:9:

| | | | | | | |
|---|---|---|---|---|---|---|
| CCTGGGTCAA | AAATTGATAT | TTAGTAAAAT | TAGTTGCACT | TTGTGCATTT | TTCATAAGA | 60 |
| TGAGTCATAT | GTTTTAAATT | GTAGTAATGA | AAAACAGTAT | TATATCATAA | TGAATTGGTA | 120 |
| TCTTAATAAA | AGAGATGGAG | GTAACTTATG | GATAACAATC | CGAACATCAA | TGAATGCATT | 180 |
| CCTTATAATT | GTTTAAGTAA | CCCTGAAGTA | GAAGTATTAG | GTGGAGAAAG | AATAGAAACT | 240 |
| GGTTACACCC | CAATCGATAT | TTCCTTGTCG | CTAACGCAAT | TTCTTTTGAG | TGAATTTGTT | 300 |
| CCCGGTGCTG | GATTTGTGTT | AGGACTAGTT | GATATAATAT | GGGGAATTTT | TGGTCCCTCT | 360 |
| CAATGGGACG | CATTTCTTGT | ACAAATTGAA | CAGTTAATTA | ACCAAGAAT | AGAAGAATTC | 420 |
| GCTAGGAACC | AAGCCATTTC | TAGATTAGAA | GGACTAAGCA | ATCTTTATCA | AATTTACGCA | 480 |
| GAATCTTTTA | GAGAGTGGGA | AGCAGATCCT | ACTAATCCAG | CATTAAGAGA | AGAGATGCGT | 540 |
| ATTCAATTCA | ATGACATGAA | CAGTGCCCTT | ACAACCGCTA | TTCCTCTTTT | GGCAGTTCAA | 600 |
| AATTATCAAG | TTCCTCTTTT | ATCAGTATAT | GTTCAAGCTG | CAAATTTACA | TTTATCAGTT | 660 |
| TTGAGAGATG | TTTCAGTGTT | TGGACAAAGG | TGGGGATTTG | ATGCCGCGAC | TATCAATAGT | 720 |
| CGTTATAATG | ATTTAACTAG | GCTTATTGGC | AACTATACAG | ATTATGCTGT | GCGCTGGTAC | 780 |
| AATACGGGAT | TAGAGCGTGT | ATGGGGACCG | GATTCTAGAG | ATTGGGTAAG | GTATAATCAA | 840 |
| TTTAGAAGAG | AGCTAACACT | TACTGTATTA | GATATCGTTG | CTCTATTCTC | AAATTATGAT | 900 |
| AGTCGAAGGT | ATCCAATTCG | AACAGTTTCC | CAATTAACAA | GAGAAATTTA | TACGAACCCA | 960 |
| GTATTAGAAA | ATTTTGATGG | TAGTTTTCGT | GGAATGGCTC | AGAGAATAGA | ACAGAATATT | 1020 |
| AGGCAACCAC | ATCTTATGGA | TATCCTTAAT | AGTATAACCA | TTTATACTGA | TGTGCATAGA | 1080 |
| GGCTTTAATT | ATTGGTCAGG | GCATCAAATA | ACAGCTTCTC | CTGTAGGGTT | TCAGGACCA | 1140 |
| GAATTCGCAT | TCCCTTTATT | TGGGAATGCG | GGGAATGCAG | CTCCACCCGT | ACTTGTCTCA | 1200 |
| TTAACTGGTT | TGGGGATTTT | TAGAACATTA | TCTTCACCTT | TATATAGAAG | AATTATACTT | 1260 |
| GGTTCAGGCC | CAAATAATCA | GGAACTGTTT | GTCCTTGATG | GAACGGAGTT | TTCTTTTGCC | 1320 |
| TCCCTAACGA | CCAACTTGCC | TTCCACTATA | TATAGACAAA | GGGGTACAGT | CGATTCACTA | 1380 |
| GATGTAATAC | CGCCACAGGA | TAATAGTGTA | CCACCTCGTG | CGGGATTTAG | CCATCGATTG | 1440 |
| AGTCATGTTA | CAATGCTGAG | CCAAGCAGCT | GGAGCAGTTT | ACACCTTGAG | AGCTCCAACG | 1500 |
| TTTTCTTGGC | AGCATCGCAG | TGCTGAATTT | AATAATATAA | TTCCTTCATC | ACAAATTACA | 1560 |
| CAAATACCTT | TAACAAAATC | TACTAATCTT | GGCTCTGGAA | CTTCTGTCGT | TAAAGGACCA | 1620 |

```
GGATTTACAG  GAGGAGATAT  TCTTCGAAGA  ACTTCACCTG  GCCAGATTTC  AACCTTAAGA   1 6 8 0
GTAAATATTA  CTGCACCATT  ATCACAAAGA  TATCGGGTAA  GAATTCGCTA  CGCTTCTACT   1 7 4 0
ACAAATTTAC  AATTCCATAC  ATCAATTGAC  GGAAGACCTA  TTAATCAGGG  TAATTTTTCA   1 8 0 0
GCAACTATGA  GTAGTGGGAG  TAATTTACAG  TCCGGAAGCT  TTAGGACTGT  AGGTTTTACT   1 8 6 0
ACTCCGTTTA  ACTTTTCAAA  TGGATCAAGT  GTATTTACGT  TAAGTGCTCA  TGTCTTCAAT   1 9 2 0
TCAGGCAATG  AAGTTTATAT  AGATCGAATT  GAATTTGTTC  CGGCAGAAGT  AACCTTTGAG   1 9 8 0
GCAGAATATG  ATTTAGAAAG  AGCACAAAAG  GCGGTGAATG  AGCTGTTTAC  TTCTTCCAAT   2 0 4 0
CAAATCGGGT  TAAAAACAGA  TGTGACGGAT  TATCATATTG  ATCAAGTATC  CAATTTAGTT   2 1 0 0
GAGTGTTTAT  CAGATGAATT  TTGTCTGGAT  GAAAAACAAG  AATTGTCCGA  GAAAGTCAAA   2 1 6 0
CATGCAAGC   GACTTAGTGA  TGAGCGGAAT  TTACTTCAAG  ATCCAAACTT  CAGAGGGATC   2 2 2 0
AATAGACAAC  TAGACCGTGG  CTGGAGAGGA  AGTACGGATA  TTACCATCCA  AGGAGGCGAT   2 2 8 0
GACGTATTCA  AAGAGAATTA  CGTTACGCTA  TTGGGTACCT  TGATGAGTG   CTATCCAACG   2 3 4 0
TATTTATATC  AAAAAATAGA  TGAGTCGAAA  TTAAAAGCCT  ATACCCGTTA  TCAATTAAGA   2 4 0 0
GGGTATATCG  AAGATAGTCA  AGACTTAGAA  ATCTATTTAA  TTCGCTACAA  TGCAAAACAT   2 4 6 0
GAAACAGTAA  ATGTGCCAGG  TACGGGTTCC  TTATGGCCGC  TTTCAGCCCA  AAGTCCAATC   2 5 2 0
GGAAAGTGTG  GAGAGCCGAA  TCGATGCGCG  CCACACCTTG  AATGGAATCC  TGACTTAGAT   2 5 8 0
TGTTCGTGTA  GGGATGGAGA  AAAGTGTGCC  CATCATTCGC  ATCATTTCTC  CTTAGACATT   2 6 4 0
GATGTAGGAT  GTACAGACTT  AAATGAGGAC  CTAGGTGTAT  GGGTGATCTT  TAAGATTAAG   2 7 0 0
ACGCAAGATG  GGCACGCAAG  ACTAGGGAAT  CTAGAGTTTC  TCGAAGAGAA  ACCATTAGTA   2 7 6 0
GGAGAAGCGC  TAGCTCGTGT  GAAAAGAGCG  GAGAAAAAAT  GGAGAGACAA  ACGTGAAAAA   2 8 2 0
TTGGAATGGG  AAACAAATAT  CGTTTATAAA  GAGGCAAAAG  AATCTGTAGA  TGCTTTATTT   2 8 8 0
GTAAACTCTC  AATATGATCA  ATTACAAGCG  GATACGAATA  TTGCCATGAT  TCATGCGGCA   2 9 4 0
GATAAACGTG  TTCATAGCAT  TCGAGAAGCT  TATCTGCCTG  AGCTGTCTGT  GATTCCGGGT   3 0 0 0
GTCAATGCGG  CTATTTTTGA  AGAATTAGAA  GGGCGTATTT  TCACTGCATT  CTCCCTATAT   3 0 6 0
GATGCGAGAA  ATGTCATTAA  AAATGGTGAT  TTTAATAATG  GCTTATCCTG  CTGGAACGTG   3 1 2 0
AAAGGGCATG  TAGATGTAGA  AGAACAAAAC  AACCAACGTT  CGGTCCTTGT  TGTTCCGGAA   3 1 8 0
TGGAAGCAG   AAGTGTCACA  AGAAGTTCGT  GTCTGTCCGG  GTCGTGGCTA  TATCCTTCGT   3 2 4 0
GTCACAGCGT  ACAAGGAGGG  ATATGGAGAA  GGTTGCGTAA  CCATTCATGA  GATCGAGAAC   3 3 0 0
AATACAGACG  AACTGAAGTT  TAGCAACTGC  GTAGAAGAGG  AAATCTATCC  AAATAACACG   3 3 6 0
GTAACGTGTA  ATGATTATAC  TGTAAATCAA  GAAGAATACG  GAGGTGCGTA  CACTTCTCGT   3 4 2 0
AATCGAGGAT  ATAACGAAGC  TCCTTCCGTA  CCAGCTGATT  ATGCGTCAGT  CTATGAAGAA   3 4 8 0
AAATCGTATA  CAGATGGACG  AAGAGAGAAT  CCTTGTGAAT  TAACAGAGG   GTATAGGGAT   3 5 4 0
TACACGCCAC  TACCAGTTGG  TTATGTGACA  AAAGAATTAG  AATACTTCCC  AGAAACCGAT   3 6 0 0
AAGGTATGGA  TTGAGATTGG  AGAAACGGAA  GGAACATTTA  TCGTGGACAG  CGTGGAATTA   3 6 6 0
CTCCTTATGG  AGGAATAGTC  TCATGCAAAC  TCAGGTTTAA  ATATCGTTTT  CAAATCAATT   3 7 2 0
GTCCAAGAGC  AGCATTACAA  ATAGATAAGT  AATTTGTTGT  AATGAAAAAC  GGACATCACC   3 7 8 0
TCCATTGAAA  CGGAGTGATG  TCCGTTTTAC  TATGTTATTT  TCTAGT                  3 8 2 6
```

( 2 ) INFORMATION FOR SEQ ID NO:10:

( i ) SEQUENCE CHARACTERISTICS:
        ( A ) LENGTH: 1176 amino acids (B) TYPE: amino acid
(C) STRANDEDNESS: single
(D) TOPOLOGY: linear (ii) MOLECULE TYPE: protein (xi) SEQUENCE DESCRIPTION: SEQ ID NO:10:

```
Met  Asp  Asn  Asn  Pro  Asn  Ile  Asn  Glu  Cys  Ile  Pro  Tyr  Asn  Cys  Leu
  1              5                    10                       15

Ser  Asn  Pro  Glu  Val  Glu  Val  Leu  Gly  Gly  Glu  Arg  Ile  Glu  Thr  Gly
              20                    25                       30

Tyr  Thr  Pro  Ile  Asp  Ile  Ser  Leu  Ser  Leu  Thr  Gln  Phe  Leu  Leu  Ser
              35                    40                       45

Glu  Phe  Val  Pro  Gly  Ala  Gly  Phe  Val  Leu  Gly  Leu  Val  Asp  Ile  Ile
       50                    55                       60

Trp  Gly  Ile  Phe  Gly  Pro  Ser  Gln  Trp  Asp  Ala  Phe  Leu  Val  Gln  Ile
 65                    70                    75                              80

Glu  Gln  Leu  Ile  Asn  Gln  Arg  Ile  Glu  Glu  Phe  Ala  Arg  Asn  Gln  Ala
                   85                    90                       95

Ile  Ser  Arg  Leu  Glu  Gly  Leu  Ser  Asn  Leu  Tyr  Gln  Ile  Tyr  Ala  Glu
              100                   105                     110

Ser  Phe  Arg  Glu  Trp  Glu  Ala  Asp  Pro  Thr  Asn  Pro  Ala  Leu  Arg  Glu
              115                   120                     125

Glu  Met  Arg  Ile  Gln  Phe  Asn  Asp  Met  Asn  Ser  Ala  Leu  Thr  Thr  Ala
              130                   135                     140

Ile  Pro  Leu  Leu  Ala  Val  Gln  Asn  Tyr  Gln  Val  Pro  Leu  Leu  Ser  Val
 145                   150                   155                            160

Tyr  Val  Gln  Ala  Ala  Asn  Leu  His  Leu  Ser  Val  Leu  Arg  Asp  Val  Ser
                   165                   170                     175

Val  Phe  Gly  Gln  Arg  Trp  Gly  Phe  Asp  Ala  Ala  Thr  Ile  Asn  Ser  Arg
              180                   185                     190

Tyr  Asn  Asp  Leu  Thr  Arg  Leu  Ile  Gly  Asn  Tyr  Thr  Asp  Tyr  Ala  Val
              195                   200                     205

Arg  Trp  Tyr  Asn  Thr  Gly  Leu  Glu  Arg  Val  Trp  Gly  Pro  Asp  Ser  Arg
 210                   215                   220

Asp  Trp  Val  Arg  Tyr  Asn  Gln  Phe  Arg  Arg  Glu  Leu  Thr  Leu  Thr  Val
 225                   230                   235                            240

Leu  Asp  Ile  Val  Ala  Leu  Phe  Ser  Asn  Tyr  Asp  Ser  Arg  Arg  Tyr  Pro
              245                   250                     255

Ile  Arg  Thr  Val  Ser  Gln  Leu  Thr  Arg  Glu  Ile  Tyr  Thr  Asn  Pro  Val
              260                   265                     270

Leu  Glu  Asn  Phe  Asp  Gly  Ser  Phe  Arg  Gly  Met  Ala  Gln  Arg  Ile  Glu
              275                   280                     285

Gln  Asn  Ile  Arg  Gln  Pro  His  Leu  Met  Asp  Ile  Leu  Asn  Ser  Ile  Thr
       290                   295                     300

Ile  Tyr  Thr  Asp  Val  His  Arg  Gly  Phe  Asn  Tyr  Trp  Ser  Gly  His  Gln
 305                   310                   315                            320

Ile  Thr  Ala  Ser  Pro  Val  Gly  Phe  Ser  Gly  Pro  Glu  Phe  Ala  Phe  Pro
              325                   330                     335

Leu  Phe  Gly  Asn  Ala  Gly  Asn  Ala  Ala  Pro  Pro  Val  Leu  Val  Ser  Leu
              340                   345                     350

Thr  Gly  Leu  Gly  Ile  Phe  Arg  Thr  Leu  Ser  Ser  Pro  Leu  Tyr  Arg  Arg
              355                   360                     365

Ile  Ile  Leu  Gly  Ser  Gly  Pro  Asn  Asn  Gln  Glu  Leu  Phe  Val  Leu  Asp
              370                   375                     380
```

-continued

```
Gly  Thr  Glu  Phe  Ser  Phe  Ala  Ser  Leu  Thr  Thr  Asn  Leu  Pro  Ser  Thr
385                      390                 395                           400

Ile  Tyr  Arg  Gln  Arg  Gly  Thr  Val  Asp  Ser  Leu  Asp  Val  Ile  Pro  Pro
               405                 410                      415

Gln  Asp  Asn  Ser  Val  Pro  Pro  Arg  Ala  Gly  Phe  Ser  His  Arg  Leu  Ser
          420                 425                           430

His  Val  Thr  Met  Leu  Ser  Gln  Ala  Ala  Gly  Ala  Val  Tyr  Thr  Leu  Arg
               435                 440                      445

Ala  Pro  Thr  Phe  Ser  Trp  Gln  His  Arg  Ser  Ala  Glu  Phe  Asn  Asn  Ile
     450                      455                 460

Ile  Pro  Ser  Ser  Gln  Ile  Thr  Gln  Ile  Pro  Leu  Thr  Lys  Ser  Thr  Asn
465                      470                 475                           480

Leu  Gly  Ser  Gly  Thr  Ser  Val  Val  Lys  Gly  Pro  Gly  Phe  Thr  Gly  Gly
                    485                 490                      495

Asp  Ile  Leu  Arg  Arg  Thr  Ser  Pro  Gly  Gln  Ile  Ser  Thr  Leu  Arg  Val
               500                 505                      510

Asn  Ile  Thr  Ala  Pro  Leu  Ser  Gln  Arg  Tyr  Arg  Val  Arg  Ile  Arg  Tyr
               515                 520                      525

Ala  Ser  Thr  Thr  Asn  Leu  Gln  Phe  His  Thr  Ser  Ile  Asp  Gly  Arg  Pro
     530                      535                 540

Ile  Asn  Gln  Gly  Asn  Phe  Ser  Ala  Thr  Met  Ser  Ser  Gly  Ser  Asn  Leu
545                      550                 555                           560

Gln  Ser  Gly  Ser  Phe  Arg  Thr  Val  Gly  Phe  Thr  Thr  Pro  Phe  Asn  Phe
                    565                 570                      575

Ser  Asn  Gly  Ser  Ser  Val  Phe  Thr  Leu  Ser  Ala  His  Val  Phe  Asn  Ser
               580                 585                      590

Gly  Asn  Glu  Val  Tyr  Ile  Asp  Arg  Ile  Glu  Phe  Val  Pro  Ala  Glu  Val
          595                 600                      605

Thr  Phe  Glu  Ala  Glu  Tyr  Asp  Leu  Glu  Arg  Ala  Gln  Lys  Ala  Val  Asn
     610                      615                 620

Glu  Leu  Phe  Thr  Ser  Ser  Asn  Gln  Ile  Gly  Leu  Lys  Thr  Asp  Val  Thr
625                      630                 635                           640

Asp  Tyr  His  Ile  Asp  Gln  Val  Ser  Asn  Leu  Val  Glu  Cys  Leu  Ser  Asp
               645                 650                      655

Glu  Phe  Cys  Leu  Asp  Glu  Lys  Gln  Glu  Leu  Ser  Glu  Lys  Val  Lys  His
               660                 665                      670

Ala  Lys  Arg  Leu  Ser  Asp  Glu  Arg  Asn  Leu  Leu  Gln  Asp  Pro  Asn  Phe
     675                      680                 685

Arg  Gly  Ile  Asn  Arg  Gln  Leu  Asp  Arg  Gly  Trp  Arg  Gly  Ser  Thr  Asp
     690                      695                 700

Ile  Thr  Ile  Gln  Gly  Gly  Asp  Asp  Val  Phe  Lys  Glu  Asn  Tyr  Val  Thr
705                      710                 715                           720

Leu  Leu  Gly  Thr  Phe  Asp  Glu  Cys  Tyr  Pro  Thr  Tyr  Leu  Tyr  Gln  Lys
                    725                 730                      735

Ile  Asp  Glu  Ser  Lys  Leu  Lys  Ala  Tyr  Thr  Arg  Tyr  Gln  Leu  Arg  Gly
               740                 745                      750

Tyr  Ile  Glu  Asp  Ser  Gln  Asp  Leu  Glu  Ile  Tyr  Leu  Ile  Arg  Tyr  Asn
          755                 760                      765

Ala  Lys  His  Glu  Thr  Val  Asn  Val  Pro  Gly  Thr  Gly  Ser  Leu  Trp  Pro
     770                      775                 780

Leu  Ser  Ala  Gln  Ser  Pro  Ile  Gly  Lys  Cys  Gly  Glu  Pro  Asn  Arg  Cys
785                      790                 795                           800

Ala  Pro  His  Leu  Glu  Trp  Asn  Pro  Asp  Leu  Asp  Cys  Ser  Cys  Arg  Asp
               805                 810                      815
```

-continued

```
Gly  Glu  Lys  Cys  Ala  His  His  Ser  His  His  Phe  Ser  Leu  Asp  Ile  Asp
               820                      825                      830
Val  Gly  Cys  Thr  Asp  Leu  Asn  Glu  Asp  Leu  Gly  Val  Trp  Val  Ile  Phe
          835                      840                      845
Lys  Ile  Lys  Thr  Gln  Asp  Gly  His  Ala  Arg  Leu  Gly  Asn  Leu  Glu  Phe
     850                           855                      860
Leu  Glu  Glu  Lys  Pro  Leu  Val  Gly  Glu  Ala  Leu  Ala  Arg  Val  Lys  Arg
865                      870                      875                      880
Ala  Glu  Lys  Lys  Trp  Arg  Asp  Lys  Arg  Glu  Lys  Leu  Glu  Trp  Glu  Thr
                885                      890                      895
Asn  Ile  Val  Tyr  Lys  Glu  Ala  Lys  Glu  Ser  Val  Asp  Ala  Leu  Phe  Val
               900                      905                      910
Asn  Ser  Gln  Tyr  Asp  Gln  Leu  Gln  Ala  Asp  Thr  Asn  Ile  Ala  Met  Ile
          915                      920                      925
His  Ala  Ala  Asp  Lys  Arg  Val  His  Ser  Ile  Arg  Glu  Ala  Tyr  Leu  Pro
     930                      935                      940
Glu  Leu  Ser  Val  Ile  Pro  Gly  Val  Asn  Ala  Ala  Ile  Phe  Glu  Glu  Leu
945                      950                      955                      960
Glu  Gly  Arg  Ile  Phe  Thr  Ala  Phe  Ser  Leu  Tyr  Asp  Ala  Arg  Asn  Val
               965                      970                      975
Ile  Lys  Asn  Gly  Asp  Phe  Asn  Asn  Gly  Leu  Ser  Cys  Trp  Asn  Val  Lys
          980                      985                      990
Gly  His  Val  Asp  Val  Glu  Glu  Gln  Asn  Asn  Gln  Arg  Ser  Val  Leu  Val
          995                      1000                     1005
Val  Pro  Glu  Trp  Glu  Ala  Glu  Val  Ser  Gln  Glu  Val  Arg  Val  Cys  Pro
     1010                     1015                     1020
Gly  Arg  Gly  Tyr  Ile  Leu  Arg  Val  Thr  Ala  Tyr  Lys  Glu  Gly  Tyr  Gly
1025                     1030                     1035                     1040
Glu  Gly  Cys  Val  Thr  Ile  His  Glu  Ile  Glu  Asn  Asn  Thr  Asp  Glu  Leu
               1045                     1050                     1055
Lys  Phe  Ser  Asn  Cys  Val  Glu  Glu  Glu  Ile  Tyr  Pro  Asn  Asn  Thr  Val
               1060                     1065                     1070
Thr  Cys  Asn  Asp  Tyr  Thr  Val  Asn  Gln  Glu  Glu  Tyr  Gly  Gly  Ala  Tyr
     1075                     1080                     1085
Thr  Ser  Arg  Asn  Arg  Gly  Tyr  Asn  Glu  Ala  Pro  Ser  Val  Pro  Ala  Asp
     1090                     1095                     1100
Tyr  Ala  Ser  Val  Tyr  Glu  Glu  Lys  Ser  Tyr  Thr  Asp  Gly  Arg  Arg  Glu
1105                     1110                     1115                     1120
Asn  Pro  Cys  Glu  Phe  Asn  Arg  Gly  Tyr  Arg  Asp  Tyr  Thr  Pro  Leu  Pro
               1125                     1130                     1135
Val  Gly  Tyr  Val  Thr  Lys  Glu  Leu  Glu  Tyr  Phe  Pro  Glu  Thr  Asp  Lys
               1140                     1145                     1150
Val  Trp  Ile  Glu  Ile  Gly  Glu  Thr  Glu  Gly  Thr  Phe  Ile  Val  Asp  Ser
          1155                     1160                     1165
Val  Glu  Leu  Leu  Leu  Met  Glu  Glu
     1170                     1175
```

BACILLUS THURINGIENSIS ISOLATES ACTIVE AGAINST LEPIDOPTERAN PESTS

This application is a continuation-in-part of application Ser. No. 07/981,048, filed Nov. 24, 1992, now abandoned.

FIELD OF THE INVENTION

The invention is related to a novel biologically pure *Bacillus thuringiensis* (*B.t.*) isolate which solely produces a CryIA(a)-like crystal delta-endotoxin having a molecular weight of about 130,000 daltons and activity against lepidopteran pests as well as a spore, crystal delta-endotoxin and/or mutant thereof. The invention also relates to insecticidal compositions obtainable therefrom. The invention further relates to methods of using the insecticidal compositions to control an insect pest(s) from the order Lepidoptera.

BACKGROUND OF THE INVENTION

Every year, significant portions of the world's commercially important agricultural crops, including foods, textiles, and various domestic plants are lost to pest infestation, resulting in losses in the millions of dollars. Various strategies have been used in attempting to control such pests.

One strategy is the use of chemical insecticides with a broad range of activity. However, there are a number of disadvantages to using such chemical insecticides. Specifically, because of their broad spectrum of activity, these insecticides may destroy non-target organisms such as beneficial insects and parasites of destructive pests. Additionally, these chemical insecticides are frequently toxic to animals and humans, and targeted pests frequently develop resistance when repeatedly exposed to such substances.

Another strategy has involved the use of biopesticides, which make use of naturally occurring pathogens to control insect, fungal and weed infestations of crops. Biopesticides comprise a bacterium which produces a toxin, a substance toxic to the pest. Biopesticides are generally less harmful to non-target organisms and the environment as a whole than chemical pesticides. The most widely used biopesticide is *Bacillus thuringiensis* (*B.t.*). *B.t.* is a widely distributed, rod shaped, aerobic and spore forming microorganism.

During its sporulation cycle, *B.t.* produces an alkali soluble protein(s) in crystal form known as a crystal delta-endotoxin(s) having a molecular weight ranging from 27-140 kd, which upon ingestion kills insect larvae. Toxic activity may reside in one or more of such crystal proteins in a given *B.t.* strain. Most delta-endotoxins are protoxins that are proteolytically converted into smaller toxic (truncated) polypeptides in the target insect midgut (Höfte and Whiteley, 1989, Microbiol. Rev. 53:242–255). The delta-endotoxins are encoded by cry (crystal protein) genes. The cry genes have been divided into six classes and several subclasses based on structural similarities and pesticidal specificity. The major classes are Lepidoptera-specific (cryI); Lepidoptera-and Diptera-specific (cryII); Coleoptera-specific (cryIII); Diptera-specific (cryIV) (Höfte and Whiteley, 1989, Microbiol. Rev. 53:242–255); Coleoptera- and Lepidoptera-specific (referred to as cryV by Tailor et al., 1992, Mol. Microbiol. 6:1211–1217); and Nematode-specific (referred to as cryV and cryVI by Feitelson et al., 1992, Bio/Technology 10:271–275).

Six cryI genes have been identified: cryIA(a), cryIA(b), cryIA(c), cryIB, cryIC, and cryID (Höfte and Whiteley, 1989, Microbiol. Rev. 53:242–255). Since cryIA(a), cryIA(b), and cryIA(c) show more than 80% amino acid identity, they are considered to be part of the cryIA group.

A number of *B.t.* strains have been isolated that have been found to be active against insect pests of the order Lepidoptera. *B.t.* subsp. kurstaki HD-1 produces bipyramidal and cuboidal crystal proteins in each cell during sporulation (Lüthy et al., in Microbial and Viral Pesticides, ed. E. Kurstak, Marcel Dekker, New York, 1982, pp.35–74); the bipyramidal crystal was found to be encoded by various cryIA genes (Aronson et al., 1986, Microbiol. Rev. 50:1–50). *B.t.* subsp. kurstaki HD-73 contains the cryIA(c) gene for its crystal delta-endotoxin (Adang et al., 1985, Gene 36:289–300). *B.t.* subsp. dendrolimus HD-7 and HD-37 contain a CryIA and a CryII protein; *B.t.* subsp. sotto contains an alkaline soluble protein that differs from the holotype CryIA(a) protein by 24 amino acids; *B.t.* subsp. subtoxicus HD-10 contains CryIA and CryIB proteins; *B.t.* subsp. tolworthi HD-121 contains CryIA and CryII proteins; *B.t.* subsp. entomocidus HD-110, 4448 contains CryIA, CryIB, and CryIB proteins; and *B.t.* subsp. aizawai HD-68 contains CryIA proteins (Höfte and Whiteley, 1989, Microbiol. Reviews 53:242–255). Bt. subsp. aizawai HD-11 contains a Cry IA protein as well as a $P_2$ crystal (Hofte and whiteley, 1989, Microbiol. Rev. 53:242–255). Padua, 1990, Microbiol. Lett. 66:257–262, discloses the isolation of two mutants containing two crystal delta-endotoxins, a 144 kD protein having activity against a lepidopteran pest and a 66 kD protein having activity against mosquitoes. Payne, U.S. Pat. No. 4,990,332, issued Feb. 5, 1993, discloses an isolate of *B.t.* PS85A1 and a mutant of the isolate, PS85A1 which both have activity against *Plutella xylostella*, a Lepidopteran pest and produce alkali soluble proteins having a molecular weight of 130,000 and 60,000 daltons. Payne, U.S. Pat. No. 5,045,469, issued Sep. 3, 1991 discloses a *B.t.* isolate designated PS81F which also produces alkali soluble proteins having a molecular weight of 130,000 and 60,000 daltons and has activity against *Spodoptera exigua* and *T. ni;* the toxin gene from PS81F appears to have little homology to the toxin gene from *B.t.* subsp. kurstaki HD-1. Payne, U.S. Pat. No. 5,206,166, filed Jun. 25, 1992, issued Apr. 27, 1993, discloses *B.t.* isolates PS81A2 and PS81RR1 which produce 133,601 and 133,367 dalton alkali-soluble proteins; both have activity against *Trichoplusia ni, Spodoptera exigua* and *Plutella xylostella* and are different from B.t subsp kurstaki HD-1 and other *B.t.* isolates. Payne, U.S. Pat. No. 5,169,629, filed Nov. 1, 1988, issued Dec. 2, 1992, discloses *B.t.* isolate PS81GG active against lepidopteran pests and which produces a bipyramidal (130,000 daltons) and a cuboidal (60,000 daltons) crystal delta-endotoxin. Payne, U.S. Pat. No. 5,188,960, filed Dec. 14, 1989, issued Feb. 23, 1993, discloses *B.t.* PS81I which produces a 130,000 dalton alkali soluble protein having a flagellar serotype of 7, aizawai which can be distinguished from HD-1 and is active against *Spodoptera exigua, Plutella xylostella,* and *Choristoneura occidentalis*. Bernier et al., U.S. Pat. No. 5,061,489 and WO 90/03434 discloses strain A20 producing a delta-endotoxin encoded by at least three genes: 6.6-, 5.3-, and 4.5-type genes (CryIA(a)-like, cryIA(b), and cryIA(c)). Bradfish et al., U.S. Pat. No. 5,208,017, discloses *B.t.* isolates PS86A1 and PS86Q3 which respectively produce alkali-soluble proteins having a molecular weight of 58,000 and 45,000 daltons and 155,000, 135,000, 98,000, 62,000, and 58,000 daltons respectively and which have activity against lepidopteran and coleopteran pests.

It is advantageous to isolate new strains of *Bacillus thuringiensis* so that there exists a wider spectrum of biopesticides for any given insect pest.

SUMMARY OF THE INVENTION

The invention is related to a novel biologically pure *Bacillus thuringiensis* strain(s) or a spore(s) or mutant (s) thereof which strain or mutant in contrast to *B.t.* strains disclosed in the prior art, solely produces a CryIA(a)-like crystal delta-endotoxin having activity against an insect pest of the order Lepidoptera and a molecular weight of about 130,000 daltons. As defined herein, a "biologically pure" *B.t.* strain is a strain essentially free of microbial contaminants. In a specific embodiment of the invention, the thuringiensis strains of the present invention are EMCC-0073 and EMCC-0074 having all of the identifying characteristics of NRRL B-21014 and NRRL B- 21015 respectively.

As defined herein, a CryIA(a)-like crystal delta-endotoxin is a protein in crystalline form substantially homologous to a CryIA(a) protein which is immunologically reactive with antibodies to the CryIA(a) protein and has essentially the same insecticidal activity as a CryIA(a) protein. Preferably, the CryIA(a)-like protein has at least 90% homology to the CryIA(a) protein; more preferably at least 95% homology and most preferably at least 99% homology.

As detailed above, the prior art strains produce crystal delta-endotoxins encoded not only by the cryIA(a) gene, but by other genes as well. The CryIA(a)-like crystal delta-endotoxin is encoded by at least one copy of a cryIA(a)-like gene. As defined herein, a "cryIA(a)-like gene" is a DNA sequence encoding a CryIA(a)-like crystal delta-endotoxin defined above. In a specific embodiment, the cryIA(a)-like gene has at least 90% homology to the cryIA(a) gene, preferably at least 95% homolgy to the cryIA(a) gene and most preferably at least 99% homolgy to the cryIA(a) gene.

The invention is also related to a substantially pure crystal delta-endotoxin. As defnded herein, a "substantially pure" crystal delta-endotoxin is substantially free (>95%) of other proteins and/or other contaminants. As will be detailed in Section 5, infra, the crystal delta-endotoxin of the present invention is obtainable from the strains of the present invention.

The novel *Bacillus thuringiensis* strains, spores, mutants or crystal delta-endotoxins may within the scope of this invention be formulated into an insecticidal composition. In one embodiment, the strain, spores, mutant or crystal delta-endotoxin may be combined with an insecticidal carrier. The insecticidal composition may be used to control an insect pest from the order Lepidoptera, particularly *Spodoptera exigua*, *Heliothis zea*, and *Heliothis virescens* in a method comprising exposing the pest to an insect-controlling effective amount of such an insecticidal composition.

DETAILED DESCRIPTION OF THE INVENTION

Figure 1:
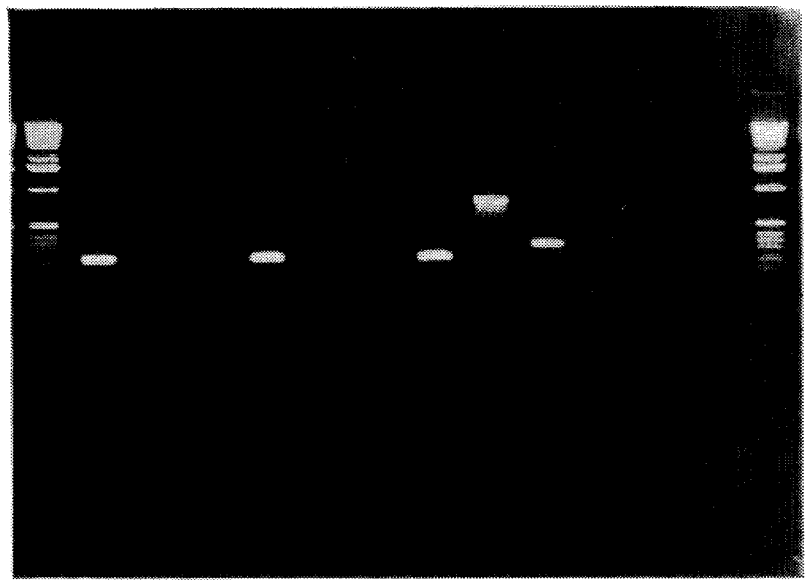
FIG. 1 shows the results of PCR analysis of *Bacillus thuringiensis* strains for cryIAgenes by agarose gel electrophoresis. Lanes 1 and 14 show molecular weight markers (1 kb ladder, Bethesda Research Laboratories). Lanes 2–4 show analysis of strain EMCC-0073 with cryIA(a), cryIA(b), and cryIA(c) oligonucleotide primers respectively; lanes 5-7 shows analysis of strain EMCC-0074 with cryIA(a), cryIA(b), and cryIA(c) oligonucleotide primers respectively; lanes 8–10 shows analysis of strain EMCC-0086 with cryIA(a), cryIA(b), and cryIA(c) oligonucleotide primers respectively; and lanes 11–13 shows analysis of a *Bacillus thuringiensis* subsp. tenebrionis strain containing only cryIIIA gene with cryIA(a), cryIA(b), and cryIA(c) oligonucleotide primers respectively. EMCC-0086 is a *Bacillus thuringiensis* subsp. kurstaki HD-1 strain containing all three cryIA genes.

The spores and crystal delta-endotoxin of the present invention are obtainable from the strains of the present invention. The strains of the present invention may be cultured using media and fermentation techniques known in the art (see, for example, Rogoff et al., 1969, J. Invertebrate Path. 14:122–129; Dulmage et al., 1971, J. Invertebrate Path. 18:353–358; Dulmage et al., in Microbial Control of Pests and Plant Diseases, H. D. Burges, ed., Academic Press, N.Y., 1980). Upon completion of the fermentation cycle, the bacteria can be harvested by separating *B.t.* spores and crystal delta-endotoxin from the fermentation broth by means well known in the art, e. g. centrifugation. The spores and crystal proteins are contained in the pellet.

Purification of the crystal delta-endotoxin can be carried out by various procedures known in the art, including but not limited to chromatography (e.g. ion exchange, affinity, hydrophobic and size exclusion), further centrifugation, electrophoretic procedures, differential solubility, or any other standard technique for the purification of proteins.

The invention is also directed to a mutant *B.t.* strain which produces a larger amount of and/or a larger crystal of CryIA(a)-like crystal delta-endotoxin than the parental strain. A "parental strain" as defined herein is the original Bacillus strain before mutagenesis. In a specific embodiment, the mutant contains more than one copy of the CryIA(a)-like gene.

To obtain such mutants, the parental strain may, for example, be treated with a mutagen by chemical means such as N-methyl-N'-nitro-N-nitrosoguanidine or ethyl methane-sulfonate, gamma-irradiation, X-ray or UV-irradiation. Specifically, in one method of mutating Bacillus strains and selecting such mutants the parental strain is:

i) treated with a mutagen;

ii) the thus treated mutants are grown in a medium suitable for the selection of a mutant strain;

iii) selection of a mutant strain.

According to a preferred embodiment of this method, the selected colonies are grown in a normal production medium, and a final selection for strains capable of increased CryIA(a)-like protein production is performed.

Alternatively, the mutant may be obtained used recombinant DNA methods known in the art. For example, a DNA sequence containing two or more copies of the CryIA(a)-like gene may be inserted into an appropriate expression vector and subsequently introduced into the parental strain using procedures known in the art.

The activity of the *B.t.* strains of the present invention or a spore(s), mutant(s) or crystal delta-endotoxin thereof against various insect pests may be assayed using procedures known in the art, such as an artificial insect diet incorporation assay, artificial diet overlay, leaf painting, leaf dip, and foliar spray. Specific examples of such assays are given in Section 6, infra.

COMPOSITIONS

The strain, spore(s), crystal delta-endotoxin, or mutant(s) of the present invention described supra can be formulated with an acceptable carrier into an insecticidal composition(s) that is for example, a suspension, a solution, an emulsion, a dusting powder, a dispersible granule, a wettable powder, an emulsifiable concentrate, an aerosol or impregnated granule.

Such compositions disclosed above may be obtained by the addition of a surface active agent, an inert carrier, a preservative, a humectant, a feeding stimulant, an attractant, an encapsulating agent, a binder, an emulsifier, a dye, a U.V. protectant, a buffer, a flow agent, or other component to facilitate product handling and application for particular target pests.

Suitable surface-active agents include but are not limited to anionic compounds such as a carboxylate, for example, a metal. carboxylate of a long chain fatty acid; an N-acylsarcosinate; mono or di-esters of phosphoric acid with fatty alcohol ethoxylates or salts of such esters; fatty alcohol sulphates such as sodium dodecyl sulphate, sodium octadecyl sulphate or sodium cetyl sulphate; ethoxylated fatty alcohol sulphates; ethoxylated alkylphenol sulphates; lignin sulphonates; petroleum sulphonates; alkyl aryl sulphonates such as alkyl-benzene sulphonates or lower alkylnaphthalene sulphonates, e.g. butyl-naphthalene sulphonate; salts of sulphonated naphthalene-formaldehyde condensates; salts of sulphonated phenol-formaldehyde condensates; or more complex sulphonates such as the amide sulphonates, e.g. the sulphonated condensation product of oleic acid and N-methyl taurine or the dialkyl sulphosuccinates, e.g. the sodium sulphonate or dioctyl succinate. Non-ionic agents include condensation products of fatty acid esters, fatty alcohols, fatty acid amides or fatty-alkyl- or alkenyl-substituted phenols with ethylene oxide, fatty esters of polyhydric alcohol ethers, e.g. sorbitan fatty acid esters, condensation products of such esters with ethylene oxide, e.g. polyoxyethylene sorbitar fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine as an acetate, naphthenate or oleate; an oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include but are not limited to inorganic minerals such as kaolin, phyllosilicates, carbonates, sulfates, phosphates or botanical materials such as cork, powdered corncobs, peanut hulls, rice hulls, and walnut shells.

The compositions of the present invention can be in a suitable form for direct application or as a concentrate or primary composition which requires dilution with a suitable quantity of water or other diluent before application. The insecticidal concentration will vary depending upon the nature of the particular formulation, specifically, whether it is a concentrate or to be used directly. The composition contains 1 to 98% of a solid or liquid inert carrier, and 0 to 50%, preferably 0.1 to 50% of a surfactant. These compositions will be administered at the labeled rate for the commercial product, preferably about 0.01 lb-5.0 lb per acre when in dry form and at about 0.01 pts-10 pts per acre when in liquid form.

In a further embodiment, the strain, spore, crystal delta-endotoxin or mutant of the present invention can be treated prior to formulation to prolong the pesticidal activity when applied to the environment of a target pest as long as the pretreatment is not deleterious to the crystal delta-endotoxin. Such treatment can be by chemical and/or physical means as long as the treatment does not deleteriously affect the properties of the composition(s). Examples of chemical reagents include but are not limited to halogenating agents; aldehydes such as formaldehyde and glutaraldehyde; anti-infectives, such as zephiran chloride; alcohols, such as isopropranol and ethanol; and histological fixatives, such as Bouin's fixative and Helly's fixative (see, for example, Humason, Animal Tissue Techniques, W.H. Freeman and Co., 1967).

The compositions of the invention can be applied directly to the plant by, for example, spraying or dusting at the time when the pest has begun to appear on the plant or before the appearance of pests as a protective measure. Plants to be protected within the scope of the present invention include but are not limited to cereals (wheat, barley, rye, oats, rice, sorghum and related crops), beets (sugar beet and fodder beet), drupes, pomes and soft fruit (apples, pears, plums, peaches, almonds, cherries, strawberries, raspberries, and blackberries), leguminous plants (alfalfa, beans, lentils, peas, soybeans), oil plants (rape, mustard, poppy, olives, sunflowers, coconuts, castor oil plants, cocoa beans, groundnuts), cucumber plants (cucumber, marrows, melons), fibre plants (cotton, flax, hemp, jute), citrus fruit (oranges, lemons, grapefruit, mandarins), vegetables (spinach, lettuce, asparagus, cabbages and other brassicae, carrots, onions, tomatoes, potatoes, paprika), lauraceae (avocados, cinnamon, camphor), deciduous trees and conifers (e.g. linden-trees, yew-trees, oak-trees, alders, poplars, birch-trees, firs, larches, pines), or plants such as maize, turf plants, tobacco, nuts, coffee, sugar cane, tea, vines hops, bananas and natural rubber plants, as well as ornamentals. In both cases, the preferred mode of application is by foliar spraying. It is generally important to obtain good control of pests in the early stages of plant growth as this is the time when the plant can be most severely damaged. The spray or dust can conveniently contain another pesticide if this is thought necessary. In a preferred embodiment, the composition of the invention is applied directly to the plant.

The compositions of the present invention may be effective against pests including but not limited to pests of the order Lepidoptera, e.g. *Achroia grisella, Acleris gloverana, Acleris variana, Adoxophyes orana, Agrotis ipsilon, Alabama argillacea, Alsophila pometaria, Amyelois transitella, Anagasta kuehniella, Anarsia lineatella, Anisota senatoria, Antheraea pernyi, Anticarsia gemmatalis, Archips sp., Argyrotaenia sp., Athetis mindara, Bombyx mori, Bucculatrix thurberiella, Cadra cautella, Choristoneura sp., Cochylls hospes, Colias eurytheme, Corcyra cephalonica, Cydia latiferreanus, Cydia pomonella, Datana integerrima, Dendrolimus sibericus, Desmia funeralis, Diaphania hyalinata, Diaphania nitidalis, Diatraea grandiosella, Diatraea saccharalis, Ennomos subsignaria, Eoreuma loftini, Ephestia elutella, Erannis tilaria, Estigmene acrea, Eulia salubricola, Eupocoellia ambiguella, Eupoecilia ambiguella, Euproctis chrysorrhoea, Euxoa messoria, Galleria mellonella, Grapholita molesta, Harrisina americana, Helicoverpa subflexa, Helicoverpa zea, Hellothis virescens, Hemileuca oliviae, Homoeosoma electellum, Hyphantria cunea, Keiferia lycopersicella, Lambdina fiscellaria fiscellaria, Lambdina fiscellaria lugubrosa, Leucoma salicis, Lobesia botrana, Loxostege sticticalis, Lymantria dispar, Macalla thyrsisalis, Malacosoma sp., Mamestra brassicae, Mamestra configurata, Manduca quinquemaculata, Manduca sexta, Maruca testulalis, Melanchra picta, Operophtera brumata, Orgyia sp., Ostrinia nubilalis, Paleacrita vernata, Papilio cresphontes, Pectinophora gossypiella, Phryganidia californica, Phyllonorycter blancardella, Pieris napi, Pieris rapae, Plathypena scabra, Platynota flouendana, Platynota stultana, Platyptilia carduidactyla, Plodia interpunctella, Plutella xylostella, Pontia protodice, Pseudaletia unipuncta, Pseudoplasia includens, Sabulodes aegrotata, Schizura concinna, Sitotroga cerealella, Spilonota ocellana, Spodoptera sp., Thaurnstopoea pityo-*

*campa, Tinsola bisselliella, Trichoplusia hi, Udea rubigalis, Xylomyges curiails,* and *Yponomeuta padella.*

The following examples are presented by way of illustration, not by way of limitation.

EXAMPLES

CULTURING OF *B.t.* STRAINS EMCC-0073 AND EMCC-0074

A subculture of EMCC-0073 and EMCC-0074, maintained on a Nutrient Broth Agar slant is used to inoculate a 250 ml baffle shake flask containing 50 ml of medium with the following composition.

| | |
|---|---|
| Corn Steep liquor | 15 g/l |
| MATLRIN ™-100 (malodextrin) | 40 g/l |
| Potato Starch | 30 g/l |
| KH$_2$PO$_4$ | 1.77 g/l |
| K$_2$HPO$_4$ | 4.53 g/l |

The pH of the medium is adjusted to 7.0 using 10 N NaOH.

After inoculation, shake flasks are incubated at 30° C. on a rotary shaker with 250 rpm shaking for 72 hours. The *B.t.* crystals and spores, obtained in the above fermentation are recovered by centrifugation at 15,000 rpm for 15 minutes using a Sorvall RC-5B centrifuge.

INSECTICIDAL ACTIVITY OF EMCC-0073 AND EMCC-0074

EMCC-0073 and EMCC-0074 are cultivated in shake flasks as described in Section 6.1., supra. A 1:50 dilution of culture broth was made. 5 ml of such diluted culture broth is transferred into a 50 ml propylene centrifuge tube. 20 ml of artificial insect diet containing antibiotics is added into the centrifuge tube. The mixture is subsequently dispensed into bioassay trays. Three to six eggs each of beet armyworm (*Spodoptera exigua*), corn earworm (*Hellothis zea*) and tobacco budworm (*Heliothis virescens*) are applied on the surface of the "diet". Mylar is ironed onto the bioassay trays and the trays were incubated at 28° C. without photoperiod. Scoring is carried out at 7 and 11 days.

At the dosage tested, EMCC-0073 and EMCC-0074 stunted *Spodoptera exigua* and *Heliothis zea*. After seven days incubation, both *Spodoptera exigua* and *Heliothis zea* only grows to less than 25% of the size of the control larvae. At the same dosage, EMCC-0073 and EMCC-0074 kills 50% and 70% respectively, of the testing population of *Heliothis virescens*. In Table I, the bioactivity of EMCC-0073 and EMCC-0074 towards *Spodoptera exigua* and *Hellothis zea* is expressed in terms of stunt score (SS). The stunt score is determined after incubating the trays for 7 days. In this system, 4=full size larvae (control larvae); 3=¾ size of control larvae; 2=½ size of control larvae; and 1=¼ size of control larvae. The smaller the number, the higher the *B.t.* activity. The bioactivity of EMCC-0073 and EMCC-0074 towards *Heliothis virescens* is determined in terms of % mortality and the live larvae (survivors) were scored by stunt score (SS) for their size.

TABLE I

| | *Spodoptera exigua* | | *Heliothis zea* | | *Heliothis virescens* | |
|---|---|---|---|---|---|---|
| | % Mort. | SS | % Mort. | SS | % Mort. | SS |
| EMCC-0073 | 0 | 1.0 | 0 | 0.8 | 50 | 0.5 |
| EMCC-0074 | 0 | 0.9 | 0 | 1.0 | 70 | 0.3 |
| Control (H$_2$O) | 0 | 4.0 | 0 | 4.0 | 0 | 4.0 |

CRY GENE PROFILE FOR EMCC-0073 AND EMCC-0074

The cry gene profile for EMCC-0073 and EMCC- 0074 is determined by using the PCR method which is described in the Perkin Elmer Cetus Gene Amp® PCR Reagent Kit literature with AmpliTaq® DNA Polymerase. The double-stranded DNA is heat-denatured and the two oligonucleotides of cryIA(a) (SEQ ID NO:i and SEQ ID NO:2), cryIA(b) (SEQ ID NO:3 and SEQ ID NO:4), or cryIA(c) (SEQ ID NO:5 and SEQ ID NO:6) are annealed at low temperature and then extended at an intermediate temperature.

The results from the PCR analysis are shown in FIG. 1 and indicate that *B.t.* strains EMCC-0073 and EMCC- 0074 contain the cryIA(a), but not the cryIA(b) nor the cryIA(c) genes. Therefore, the crystal delta-endotoxin of *B.t.* strains EMCC-0073 and EMCC-0074 is encoded only by the cryIA(a) gene.

Oligonucleotide primers for Polymerase Chain Reaction (PCR) amplification of the entire cryIA(a)-like gene of EMCC-0073 were designed based on the sequence of the holotype cryIA(a) gene cloned from *Bacillus thuringiensis* subsp. kurstaki HD-1 (Schnepf et al., 1985, J. Biol. Chem. 260:6264–6272). The primers are shown in the Sequence Listing as SEQ ID NO:7 and SEQ ID NO:8. Fragments bearing the cryIA(a)-like gene of EMCC-0073 (corresponding to nucleotides 380 to 4205 of the sequence reported by Schnepf et al., 1985, J. Biol. Chem. 260:6264–6272) were cloned from two separate PCRs were cloned in pCR™II (Invitrogen Corporation) or pBCSK+ (Stratagene Cloning Systems) from two separate PCRs. DNA sequencing was performed on the two clones using the Applied Biosystems 373A DNA Sequencer and PRISM Ready Reaction DyeDeoxy Terminator Cycle Sequencing Kit with synthetic oligonucleotides based on the sequence of the holotype cryIA(a) gene. The clones shared two nucleotide differences relative to the holotype cryIA(a) gene (C to T at nt 756 and C to G at nt 3551, according to the numbering of Schnepf et al., 1985, J. Biol. Chem. 260:6264–6272), which corresponded to two amino acid changes relative to the holotype CryIA(a) protoxin (Pro to Leu at residue 77 and Leu to Val at residue 1009). The nucleotide sequence is shown in the Sequence Listing as SEQ ID NO:9 and the amino acid sequence is shown in the Sequence Listing as SEQ ID NO:10.

INSECTICIDAL ACTIVITY OF PURIFIED SPORES FROM EMCC-0073

The *B.t.* culture obtained from Section 6.1., supra is transferred into sterile 250 ml centrifuge bottles and centrifuged at 10,000 rpm in a Sorvall RC-5B centrifuge for 30 minutes at 5° C. to collect crystals and spores. Pellets are then washed three times with sterile, de-ionized water. The pellets are resuspended into deionized water to i g. wet weight per 10 ml followed by sonicating the suspension on ice to disrupt any clumping. Each 10 ml suspension is further diluted to 33.2 ml with deionized water. 10 ml 3M NaCl, 23.4 ml 20% polyethylene glycol, and 33.4 ml 20% sodium dextran sulfate are all added and mixed well in a separatory funnel with the previously diluted suspension (33.2 ml). An additional 100 ml 20% polyethylene glycol is then added to the separatory funnel and the mixture is shaken vigorously to mix the phases. The phase separation of the mixture is achieved by gravity at room temperature for 30 minutes. The upper phase consists of large quantities of spores which could be removed by pipetting.

Purified spores are then bioassayed against *Spodoptera exigua*, by using the diet incorporation bioassay described in Section 6.2., supra. The results are shown in Table II. 48 second instar larvae are used for each point. Mortality is recorded on the seventh day post-treatment.

TABLE II

| μg/g of Diet | % Mortality | |
|---|---|---|
| | EMCC-0073 | EMCC-0086 |
| 83.3 | 48 | 27 |
| 55.6 | 21 | 17 |
| 35.7 | 28 | 8 |
| 22.7 | 10 | 7 |

The spores from EMCC-0073 has significantly higher activity against Spodoptera exigua than spores from the B.t.k. type of reference strain (EMCC-0086).

DEPOSIT OF MICROORGANISMS

The following strains of *Bacillus thuringiensis* have been deposited in the Agricultural Research Service Patent Culture Collection (NRRL), Northern Regional Research Center, 1815 University Street, Peoria, Ill., 61604, USA.

| Strain | Accession Number | Deposit Date |
|---|---|---|
| EMCC-0073 | NRRL B-21014 | November 16, 1992 |
| EMCC-0074 | NRRL B-21015 | November 16, 1992 |

The strains have been deposited under conditions that assure that access to the culture will be available during the pendency of this patent application to one determined by the Commissioner of Patents and Trademarks to be entitled thereto under 37 C.F.R. §1.14 and 35 U.S.C. §122 and under conditions of the Budapest Treaty. The deposit represents a biologically pure culture of each deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. A biologically pure *Bacillus thuringiensis* strain or a spore of said strain, wherein said strain is Bacillus having all the identifying characteristics of *Bacillus thuringiensis* NRRL B-21014 or *Bacillus thuringiensis* NRRL B-21015.

2. An insecticidal composition comprising the biologically pure strain of claim 1 and an insecticidal carrier.

3. A method for controlling an insect pest of the order Lepidoptera comprising applying to the pest to an insect-controlling effective amount of the insecticidal composition of claim 2.

* * * * *

UNITED STATES PATENT AND TRADEMARK OFFICE
CERTIFICATE OF CORRECTION

PATENT NO. : 5,556,784
DATED : September 17, 1996
INVENTOR(S) : C. Liu

It is certified that error appears in the above-indentified patent and that said Letters Patent is hereby corrected as shown below:

Column 1, line 51, change "H6fte" to --Höfte--.

Column 3, line 53, change "cryIAgenes" to --cryIA genes--.

Column 7, line 1, change "*Tinsola*" to --*Tineola*--.

Column 8, line 20, change "NO:i" to --NO:1--.

Column 8, line 67, change "i g." to --1 g.--.

Column 21, line 62, delete "wherein said strain is Bacillus".

Column 22, line 61, delete the second occurrence of "to".

Signed and Sealed this

First Day of April, 1997

Attest:

BRUCE LEHMAN

*Attesting Officer*  Commissioner of Patents and Trademarks